US010368795B2

United States Patent
Patwardhan (10) Patent No.: US 10,368,795 B2
(45) Date of Patent: Aug. 6, 2019

(54) ACNE IMAGING METHODS AND APPARATUS

(71) Applicant: Canfield Scientific, Incorporated, Fairfield, NJ (US)

(72) Inventor: Sachin V. Patwardhan, Morris Plains, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 208 days.

(21) Appl. No.: 14/686,824

(22) Filed: Apr. 15, 2015

(65) Prior Publication Data

US 2015/0374277 A1   Dec. 31, 2015

Related U.S. Application Data (60) Provisional application No. 62/018,866, filed on Jun. 30, 2014.

(51) Int. Cl.
  *A61B 5/00*   (2006.01)

(52) U.S. Cl.
  CPC ............ *A61B 5/445* (2013.01); *A61B 5/0013* (2013.01); *A61B 5/0022* (2013.01);
  (Continued)

(58) Field of Classification Search
  CPC ..... A61B 5/445; A61B 5/7203; A61B 5/7246; A61B 5/00222; A61B 2576/02;
  (Continued)

(56) References Cited

U.S. PATENT DOCUMENTS

| 5,760,407 | A   |   | 6/1998  | Margosiak et al. |
| 6,571,003 | B1  | * | 5/2003  | Hillebrand ............ A61B 5/0064 382/100 |
| 8,290,257 | B2  | * | 10/2012 | Demirli ................. A61B 5/441 382/128 |
| 8,472,682 | B2  | * | 6/2013  | Guissin .............. G06K 9/00369 382/128 |

(Continued)

FOREIGN PATENT DOCUMENTS

| WO | 1998024360 A1 | 6/1998 |
| WO | 1999066830 A1 | 12/1999 |
| WO | 2014047712 A1 | 4/2014 |

OTHER PUBLICATIONS

International Search Report and Written Opinion of International Searching Authority, PCT/US2015/033125, dated Aug. 10, 2015.

*Primary Examiner* — Navin Natnithithadha
*Assistant Examiner* — Andrey Shostak
(74) *Attorney, Agent, or Firm* — Brosemer, Kolefas & Assoc. LLC (57) ABSTRACT

In an arrangement for detecting acne, particularly in its earliest stages before any humanly visible or palpable manifestations thereof have emerged, a green fluorescence image of skin illuminated with blue light is captured and processed to detect the presence of microcomedones. After correcting the green fluorescence image for the non-uniform distribution of excitation light on the skin, fluorescent spots are detected therein. The subset of fluorescent spots having an intensity lower than an intensity threshold and an area smaller than an area threshold are selected as representing candidate microcomedones. The subset can be further refined by eliminating fluorescent spots having irregular shapes, are associated with inflammation, or exhibit comedone features. Additional filtering can be applied by selecting those spots whose locations correspond to pore locations. A dermatoscope with a blue illumination source and a green-filtered viewer allows live imaging of skin spots indicative of acne, including microcomedones not otherwise visible.

23 Claims, 4 Drawing Sheets

(52) U.S. Cl.
CPC .......... *A61B 5/0071* (2013.01); *A61B 5/0077* (2013.01); *A61B 5/443* (2013.01); *A61B 5/444* (2013.01); *A61B 5/7203* (2013.01); *A61B 5/7246* (2013.01); *A61B 5/742* (2013.01); *A61B 2576/02* (2013.01)

(58) Field of Classification Search
CPC ....... A61B 5/444; A61B 5/742; A61B 5/0013; A61B 5/0077; A61B 5/0071; A61B 5/443; A61B 5/441
See application file for complete search history.

(56) References Cited

U.S. PATENT DOCUMENTS

| | | | |
|---|---|---|---|
| 2002/0090123 A1* | 7/2002 | Bazin | A45D 44/005 382/128 |
| 2004/0174525 A1* | 9/2004 | Mullani | A61B 5/0059 356/369 |
| 2005/0195316 A1 | 9/2005 | Kollias et al. | |
| 2006/0092315 A1 | 5/2006 | Payonk et al. | |
| 2008/0180950 A1* | 7/2008 | Kang | A61B 5/0059 362/249.16 |
| 2009/0054744 A1* | 2/2009 | Kitamura | A61B 5/0082 600/306 |
| 2009/0137908 A1 | 5/2009 | Patwardhan | |
| 2009/0299268 A1* | 12/2009 | Anderson | A61K 8/44 604/20 |
| 2013/0006118 A1* | 1/2013 | Pan | A61N 5/0616 600/476 |
| 2017/0202504 A1* | 7/2017 | Suzuki | A61B 5/443 |

\* cited by examiner

ACNE IMAGING METHODS AND APPARATUS

RELATED PATENT APPLICATIONS

The present application claims priority from U.S. Provisional Patent Application No. 62/018,866, filed Jun. 30, 2014 and incorporated herein by reference in its entirety.

FIELD OF THE DISCLOSURE

The present disclosure relates to skin imaging and analysis, and more particularly to the imaging and analysis of skin for detecting skin conditions such as acne.

BACKGROUND INFORMATION

Acne is a common skin condition that is characterized by areas of seborrhea (scaly red skin), comedones (blackheads and/or whiteheads), pimples (papules and/or pustules), and possibly scarring. A person may display some or all of these features at once or over a period of time as multiple lesions transition through the different stages of development.

Acne begins as the result of the abnormal regulation of cells within a hair follicle, including the overstimulation of the sebaceous gland of the follicle to produce excess sebum. This causes the formation of what is referred to as a microcomedone. Once the microcomedone forms, it impedes the removal of dead skin cells and sebum from the pore. The resultant collection of dead skin cells and sebum creates an environment that is conducive to the growth and multiplication of propionbacterium acnes (P. acnes) bacteria. It is important to note that microcomedones cannot be seen or felt, in which case a conventional examination of the skin, even by an experienced dermatologist, will not reveal their presence.

As the P. acnes bacteria grow and multiply, the microcomedone grows and becomes a closed comedone or white head. Then, as the top of the white head opens, an open comedone or blackhead forms. The characteristic dark color of the blackhead results from the oxidation of melanin present in the sebum as it is exposed to air.

As the bacteria grow and multiply in the plugged follicle, they release substances that attract white blood cells, which in turn release compounds that induce inflammation. This causes a papule, which typically appears as a red bump on the surface of the skin.

As the bacteria continue to multiply and grow, more white blood cells are attracted to the follicle, causing further inflammation. The papule thus becomes a pustule and appears as an enlarging red bump with a white center. If the wall of the follicle ruptures, a larger lesion occurs. This is considered to be a large, very inflamed pimple on its way to becoming a cyst or nodule. Scarring may also result.

Treatment of acne typically depends on its severity and ranges from routine cleansing and the topical application of cleansers to the drainage of large pimples and cysts, the application of antibiotic gels, creams, or lotions, prescription retinoids, and the oral administration of antibiotics and retinoids.

Generally, to obtain the maximum benefit of treatment and to minimize damage to the skin from acne, treatment should be started as early as possible in the development of acne. Unfortunately, effective early detection or prediction of acne development is currently lacking, particularly since the early stages of acne, as characterized by microcomedones, are not visible or palpable.

SUMMARY OF THE DISCLOSURE

Embodiments of methods and apparatus in accordance with the present disclosure address the aforementioned problems by providing the ability to detect the development of acne in its early stages, particularly in the microcomedone stage.

In exemplary embodiments of methods and apparatus in accordance with the present disclosure, an image of skin illuminated with a blue light is captured via a green filter. The captured image is further processed and analyzed to detect the presence of microcomedones. A further image based on the captured image is generated, highlighting potential microcomedones in the subject skin.

The present disclosure also provides an exemplary dermatoscopic device that can be used to visualize microcomedones. In an exemplary embodiment, a handheld dermatoscope has a blue illumination source and a green filtered viewer through which skin illuminated with blue light can be viewed by a user. Microcomedones will appear through the dermatoscope as small, regularly-shaped bright spots.

The above and other aspects and features of the present disclosure will be apparent from the drawings and detailed description which follow.

DETAILED DESCRIPTION

Figure 1:
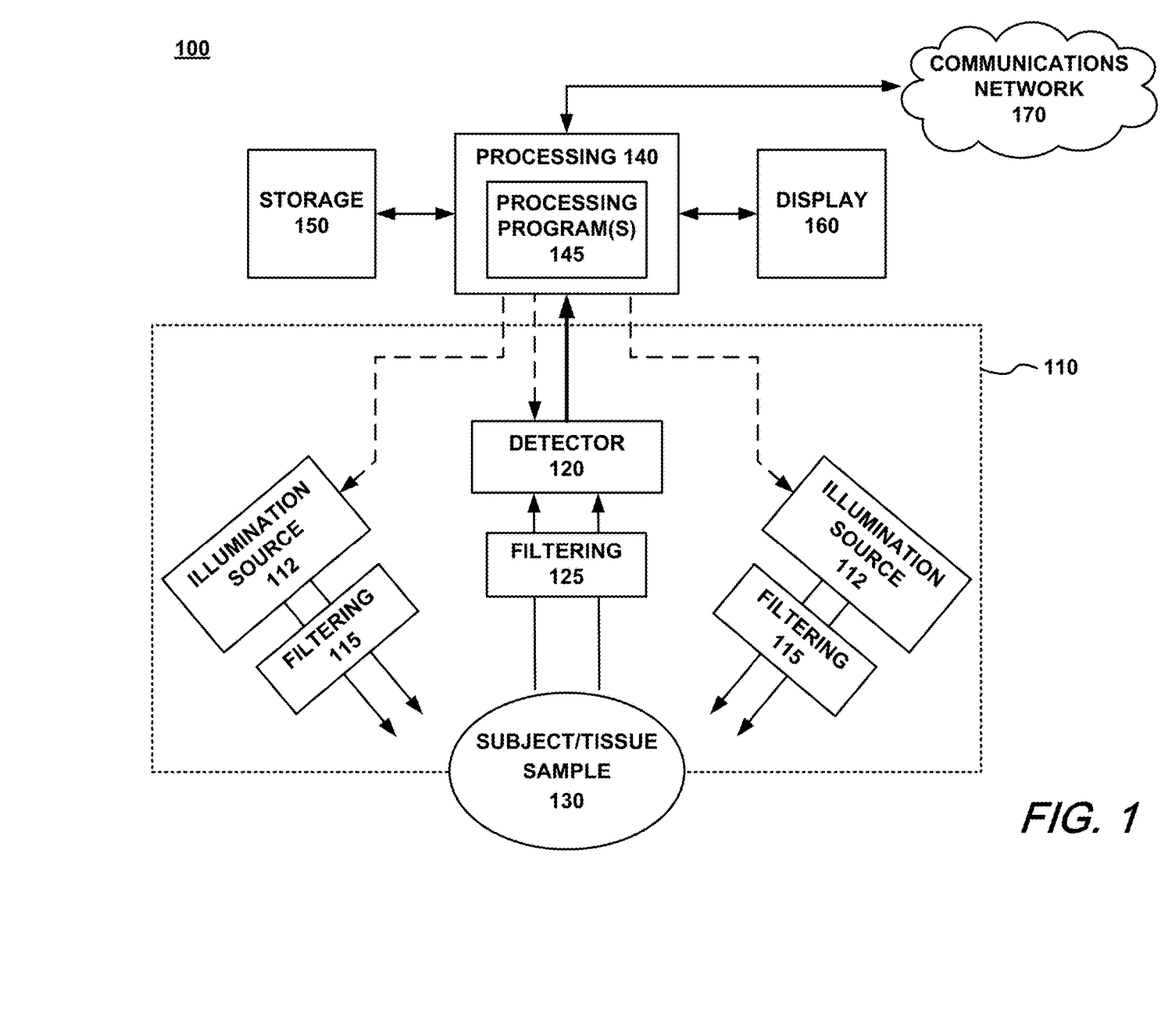
FIG. 1 is a schematic representation of an exemplary tissue imaging and processing system.

FIG. 1 schematically depicts an exemplary embodiment of a tissue imaging and processing system 100 for capturing and processing images of skin in accordance with the present disclosure.

The major components of system 100 include an imaging apparatus 110 coupled to a processing block 140. Imaging apparatus 110 may include a wide variety of systems and/or devices such as, for example, a digital camera, preferably with flash, and/or a closed environment imaging booth. Image data captured by imaging apparatus 110 is provided to processing block 140 for processing. Processing block 140 may also control imaging apparatus 110, such as by controlling the capture of images and/or illumination. Imaging apparatus 110 may also operate without being controlled by processing block 140, and only provide image data for processing. In an exemplary embodiment, system 100 provides illumination, image capture, and processing for detecting microcomedones, as described in greater detail below.

As shown in FIG. 1, imaging apparatus 110 includes one or more illumination sources 112 which are activated to shine light onto a subject's skin 130 through a respective filtering element 115. Light reflected or emitted from the subject tissue 130 is captured by a detector 120 through a filtering element 125. Each filtering element 115, 125 may include one or more filters for passing or blocking light of a selected wavelength or band of wavelengths, and/or polarizers, collectively "filters," which can be selectively placed in or out of the respective optical path of the filtering element. Note that the term "light" as used herein is not necessarily limited to humanly visible electromagnetic radiation, and may include portions of the electromagnetic spectrum above and below the visible range.

In exemplary embodiments, detector 120 may comprise a camera, such as a conventional digital SLR camera or the like, a digital video camera, or multiple one- or two-dimensional detectors, with similar or different characteristics. Multiple detectors 120 can be arranged to capture two- or three-dimensional images. The information and/or images captured by detector 120 are provided to processing block 140 for image processing as described in greater detail below. Processing block 140 may be implemented, for example, with one or more computers, workstations, or the like, operating in accordance with one or more programs 145 embodied in a compatible machine-readable medium. Processing block 140 may be coupled to a storage 150 and a display 160. Processing block 140 may also be connected to a communications network 170, such as the Internet, for transmitting images and data, and/or receiving commands, software updates or the like.

In an exemplary embodiment, system 100 is a VISIA-CR imaging system from Canfield Scientific, Inc. Detector 120 is a conventional DSLR camera, illumination sources 112 are xenon flashes, each of filtering elements 115 includes a blue-pass filter, and filtering element 125 includes a green-pass filter.

Figure 2:
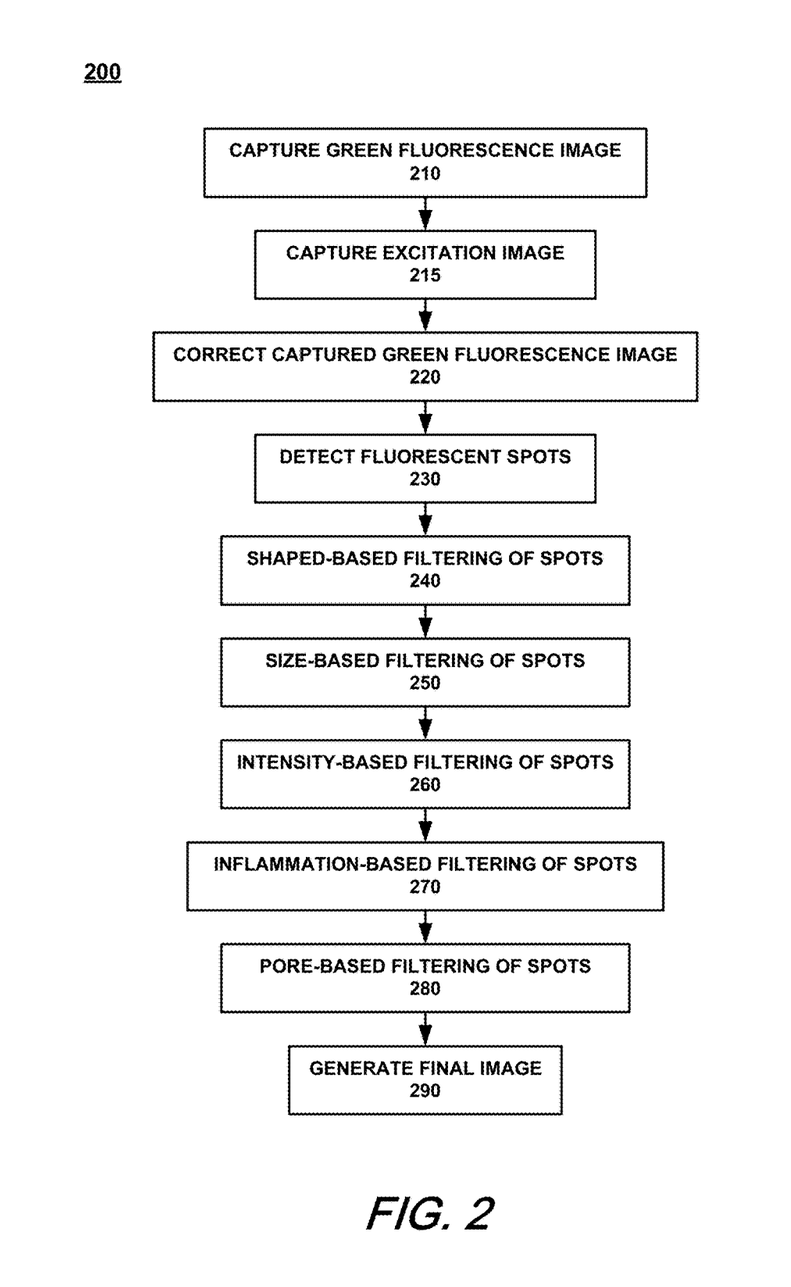
FIG. 2 is a flow chart depicting an exemplary method of detecting microcomedones in skin.

FIG. 2 is a high-level flow chart providing an overview of an exemplary method 200 of detecting microcomedones in accordance with the present disclosure. The method 200 can be carried out, for example, using system 100 of FIG. 1, with processing block 140 thereof operating in accordance with processing program(s) 145. As described in greater detail below, small and/or less bright, generally circular fluorescence spots that are not located inside inflamed areas are deemed to be microcomedones. Spots within inflamed areas that do not appear raised (characteristic of inflammatory lesions) and do not have comedone-like features (e.g., a dark enlarged pore or a whitish bump) are also deemed to be microcomedones.

In exemplary method 200, microcomedones are detected by detecting the presence of coproporphyrin III, a porphyrin that is associated with the P. acnes bacteria present in microcomedones, as well as in comedones. To detect coproporphyrin III in skin, the subject skin is illuminated with an excitation light of a selected wavelength which causes the coproporphyrin III to fluoresce with a characteristic spectral response. A selected portion of the spectral band of the light thus emitted is sensed, with the detection of a signal above a given threshold value being indicative of the presence of coproporphyrin III. The fluorescence intensity is indicative of the concentration of the fluorophore and thus of the extent of bacterial activity. In accordance with principles of the present disclosure, the wavelength of the excitation light and the portion of the spectral band used to detect emissions from the subject skin are selected so as to optimize the sensitivity to coproporphyrin III, or rather the signal-to-noise ratio thereof: i.e., the ratio of the coproporphyrin III fluorescence emission signal to the noise due to other emissions from the subject skin that may also be captured. Doing so may entail using excitation light of wavelengths other than the excitation peak wavelength of coproporphyrin III and detection filtering at wavelengths other than the emission peak wavelength of coproporphyrin III. More specifically, coproporphyrin III has a distinctive fluorescence maximum at a wavelength of approximately 615 nm. We have discovered, however, that due to the fluorescence of other fluorophores, such as protoporphyrin IX, at or about the same wavelength, and due to the limitations of the filtering that is possible, attempting to detect coproporphyrin III at or about its peak emission wavelength provides an inadequate signal-to-noise ratio, at least for the purposes of detecting microcomedones. Additionally, when using a conventional color camera employing Bayer filters, the emission peak of coproporphyrin III falls between the responses of the Green and Red Bayer filters, making it further difficult to separate it from the emission signal of protoporphyrin IX.

As shown in FIG. 2, the exemplary method 200 begins at step 210 in which an image of an area of skin is captured. In an exemplary embodiment, the subject area is illuminated with blue light, having a center wavelength of 400-410 nm and a full width at half maximum (FWHM) bandwidth of +/−5 nm to +/−20 nm. The image of the blue illuminated skin is captured through a green filter having a center wavelength of 540-560 nm and a FWHM bandwidth of +/−15 to +/−30 nm. For purposes of this description, the captured image is referred to as a green fluorescence image. With reference to FIG. 1, the blue excitation light can be generated by illumination sources 112 with filtering elements 115 selected in accordance with the aforementioned parameters and detection can be done through filtering element 125 providing the above specified green filtering.

Additionally, at or near the same time that the green fluorescence image is captured, an excitation image is captured at 215. The excitation image is captured with no filtering (125) in front of the image detector (120). The image captured is thus a total reflectance/absorbance image of the excitation wavelength by the subject skin.

Once the green fluorescence image and the excitation image have been captured, operation proceeds to step 220 in which the green fluorescence image is corrected for the non-uniform distribution of excitation light shone upon the surface of the subject skin by the illumination source. This can be done by normalizing the captured green fluorescence image against the excitation image captured in step 215. Preferably before or as part of the normalization operation, the excitation and green fluorescence images are registered with each other such as with the use of known elastic registration techniques to compensate for any movement or deformation of the subject skin between images.

In exemplary embodiments, the green fluorescence image may also be corrected for the heterogeneous tissue absorption of the excitation and emission light by chromophores in the skin, such as melanin and hemoglobin. This can be done by generating a chromophore absorption distribution image and normalizing the captured green fluorescence image against the chromophore absorption distribution image. Correcting for the non-uniform distribution of excitation light on the skin's surface and the heterogeneous tissue absorption of the excitation and emission light, provides more accurate fluorescence information that allows for more sensitive detection of coproporphyrin III, the fluorophore of interest for acne.

In exemplary embodiments, normalizing the captured green fluorescence image against the excitation image captured in step 215 will also suffice for purposes of correcting the green fluorescence image for melanin absorption. With melanin, absorption is greater at shorter wavelengths and drops exponentially with longer wavelengths. As such, while absorption by melanin at the blue excitation wavelength may be meaningful, it is much less so at the green emission wavelength and can be ignored. Correcting the fluorescence image using the excitation image, therefore, provides correction for uneven light distribution as well as for absorption by melanin.

In exemplary embodiments, correcting the captured green fluorescence image for hemoglobin absorption is optional. Typically, the blue excitation light will not penetrate deeply enough into the skin to reach the typical depth of hemoglobin and thus be absorbed thereby. The emission sought to be captured, however, is in the spectral region where hemoglobin absorption is maximum. As an early stage of acne development, however, microcomedones are non-inflammatory, in that there is no inflammation, and thus no hemoglobin, associated with them. As such, unless proximate to an inflammatory lesion such as a papule or pustule or within an area of inflammation, a microcomedone's fluorescence emission will not be significantly absorbed by hemoglobin and correction for hemoglobin absorption can be foregone. However, for subjects who present with inflammatory lesions or more wide-spread inflammation, hemoglobin absorption correction can be used in order to improve the detectability of microcomedones that may otherwise be masked by the presence of hemoglobin due to inflammation. Techniques for correcting the captured fluorescence image by normalizing it against light distribution and tissue absorption are described in U.S. Pat. No. 8,849,280, incorporated herein by reference in its entirety.

After step 220, operation then proceeds to step 230 in which the corrected green fluorescence image is processed to detect fluorescent spots therein. The fluorescent spots will appear brighter than the surrounding skin and can be detected in the image by any of a variety of known techniques. In an exemplary embodiment, detection of the fluorescent spots is done using a Top-hat filter with one or more structuring elements. The Top-hat filter provides a response that is dependent on how close the shape of an object is to the shape of the structuring element, and on the contrast of the object to the background. For each of the structuring elements, the Top-hat filter returns an image with objects that are smaller than the structuring element and brighter than their surroundings. The images returned by the top-hat filter are then thresholded for appropriate sensitivity in order to keep only those objects that are detected with a confidence at or above a threshold confidence level. In an exemplary embodiment, three disc-shaped structuring elements of different sizes are used (e.g., 24, 16 and 8 pixels radius, for an image resolution of 650 pixels/in, with threshold confidence levels of 0.4-0.6, 0.15-0.5 and 0.15-0.5, respectively). In an exemplary embodiment, the threshold levels are skin-type dependent, as different skin types will exhibit different fluorescence background levels.

Preferably, the detection of fluorescent spots is performed within an area of interest (AOI) within the corrected green fluorescence image. The AOI can be delineated automatically, such as with an automated masking operation, and/or manually, in which a user designates the AOI (such as by drawing it on the captured image using a suitable GUI, for example) or makes adjustments to an automatically determined AOI or mask area. Preferably, the AOI or mask area is selected so as to eliminate features such as eyes, lips and hair. The AOI may also be drawn to analyze only a certain portion of the image or to exclude a certain portion of the image. For example, an AOI may be designated so as to exclude the subject's nose, or to analyze only the subject's cheek(s). Multiple AOIs can be designated within the same image and each AOI analyzed individually, yielding AOI-specific analysis results, thereby making it possible, for example, to report measurements from various facial zones. Techniques for generating masks and delineating AOIs are described in U.S. Pat. Nos. 8,218,862 and 8,290,257, incorporated herein by reference in their entireties.

The fluorescent spots will appear as areas of brightness within the corrected green fluorescence image and will vary in size and intensity from spot to spot. Typically, a subset of the fluorescent spots represent microcomedones, while other fluorescent spots may represent a variety of other features, both non-inflammatory (e.g., open or closed comedones) and inflammatory (e.g., papules, pustules, nodules, cysts). Additionally, dry skin flakes and pus may also appear as bright spots in the corrected green fluorescence image. Those features, however, are typically relatively large and irregular in shape. Microcomedones and comedones, being confined to pores, appear relatively round by comparison.

It is contemplated that some fluorescent spots, particularly the smallest spots, will be due to noise or other unwanted features (e.g., lint, skin flakes) and thus should be excluded from further consideration. Accordingly, in an exemplary embodiment, any spots smaller than a threshold minimum size (e.g., 150 microns diameter, or 12 pixels in area, given a resolution of 650 pixels/inch) are discarded from the set of spots that may represent microcomedones.

Operation then proceeds to step 240 in which a shape-based filtering operation is applied to the spots identified in step 230. In an exemplary embodiment, the shapes of the spots identified in step 230 are analyzed for roundness using any of a variety of suitable techniques. Irregularly shaped spots, such as those due to dry skin flakes and pus, are eliminated from the set of spots identified in step 230. The subset of spots whose shapes are relatively round is determined and saved for further consideration as possible microcomedones. In an exemplary embodiment, the circularity and/or aspect ratio of each of the spots identified in step 230 is determined, such as by calculation, and compared to a threshold value. Any spots having a circularity greater than the threshold value are saved for further consideration. In an exemplary embodiment, such spots are determined to be those spots that meet at least one of the following conditions:

$$4\pi A/P^2 \geq 0.7, \tag{1}$$

$$L_{minor}/L_{major} \geq 0.7, \tag{2}$$

where A is the area of the spot, P is its perimeter, $L_{minor}$ is the length of its minor axis, and $L_{major}$ is the length of its major axis. Any spots not meeting one or both of the above conditions are dropped from further consideration as possible microcomedones.

Operation then proceeds to step 250 in which a size-based filtering operation is applied to the spots identified in step 240. In an exemplary embodiment, the areas of the spots identified in step 240 are compared against a threshold area value. The subset of spots whose sizes are smaller than the threshold area value is determined and saved for further consideration as possible microcomedones. In an exemplary embodiment, the threshold area value may be fixed (e.g., 90+/−30 pixels, given a resolution of 650 pixels/inch) or may be subject-dependent. For example, the threshold area value can be selected in accordance with the mean or median pore size of the subject skin being imaged. Pore size can be determined or estimated in a variety of ways, including, for example, from a database based on skin type, from a standard white light reflection image of the subject, and/or from the green fluorescence image itself. As the spots remaining after the shape-based filtering of step 240 are most likely representative of microcomedones and comedones and thus confined to pores, in an exemplary embodiment the threshold area value is selected preferably to be 80% (+/−10%) of the median and/or 130% (+/−10%) of the mean size of the subset of spots remaining after the shape-based filtering operation of step 240.

Operation then proceeds to step 260 in which an intensity-based filtering operation is applied to the spots identified in step 250. Fluorescence intensity is proportional to the concentration of the fluorophore, which in the case of coproporphyrin III is dependent on bacterial activity. Spots of a higher intensity indicate higher bacterial activity and should be classified as comedones, as opposed to microcomedones. Thus in addition to being smaller, microcomedones have lower fluorescence intensities compared to comedones.

In an exemplary embodiment, the intensities of the spots identified in step 260 are compared against a threshold intensity value. The subset of spots whose intensities do not exceed the threshold intensity value is determined and saved for further consideration as possible microcomedones. In an exemplary embodiment, the intensity of each candidate spot is determined by calculating the mean or median intensity of those image pixels associated with the spot, and the threshold intensity value is preferably 70% (+/−10%) of full scale intensity.

Operation then proceeds to step 270 in which an inflammation-based filtering operation is applied to the set of candidate spots remaining after step 260. Spots that are associated with inflammation are typically representative of inflammatory lesions and thus well beyond the microcomedone stage. As such, spots not within areas of inflammation are retained in step 270 in the set of candidate microcomedone spots. It is possible, however, for microcomedones to be found within areas of inflammation due to other conditions, or to be in close proximity to inflammatory lesions. As such, before a spot within an area of inflammation is removed from further consideration as a microcomedone, the spot is preferably analyzed to determine whether or not it has the features of a more advanced lesion, such as a shiny whitish bump in the case of a closed comedone, a dark enlarged pore in the case of an open comedone, or a raised surface in the case of an inflammatory lesion. If not, the spot is retained in the set of candidate microcomedones. A more detailed description of an exemplary inflammation-based filtering operation is described below with reference to FIG. 3.

After the inflammation-based filtering operation of step 270, operation proceeds to step 280 in which a pore-based filtering operation is carried out. Methods and apparatus for detecting pores are known, such as that provided for the VISIA imaging system, among other possibilities. In an exemplary embodiment, pores are detected using a shadow-based approach, in which shadows cast in the pores are detected in a flat-lit standard white light reflection image. For relatively dry skin, a parallel-polarized image can also be used for this purpose as it tends to better show the texture of the skin including pores. However, because a parallel-polarized image will also be sensitive to specular reflection, it may be sub-optimal for oily skin conditions, typical where acne is present. In any case, the image used for pore detection and the green fluorescence image (or an image derived therefrom) preferably are elastically registered.

The locations of the detected pores are compared to the locations of the fluorescent spots in the set of candidate microcomedone spots remaining after step 270. Any spot in the aforementioned set whose location corresponds to that of a pore is deemed to be a microcomedone, whereas any spot whose location does not correspond to a pore is not and is removed from the set.

Once the captured green fluorescence image has been processed as described above, a final image is generated at step 290 showing those spots deemed to be microcomedones. The final image can then displayed, such as on display 160, highlighting the locations of the microcomedones thus determined. The image can also be overlayed onto a standard white light image of the subject skin so as to allow a viewer of the image to see the suspected microcomedones in relation to facial features that are readily visible to the naked eye. The image can be used, for example, to direct the application of one or more treatments, among other uses.

The resultant image of method 200 can be used and/or further processed to extract additional information or to determine one or more metrics indicative of the condition of the imaged skin. For example, the number of microcomedones and/or comedones in the captured and/or processed fluorescence image, or portions thereof, can be counted to provide a metric indicative of the condition of the skin. The original and processed images and/or associated information can be displayed, such as on display 160, stored, such as in storage 150, and/or communicated, such as over network 170. Stored images and/or live images and/or their associated information can be compared to determine the efficacy of treatments or other measures.

It should be noted that various steps of method 200 may be combined, re-ordered, performed in parallel, or eliminated in some cases. For example, the shaped-based filtering performed in step 240 may be combined with the size-based filtering performed in step 250, since both may entail determining the sizes of spots. Inflammation-based filtering step 270 can be performed before size-based filtering step 250. Or, intensity-based filtering step 260 may be performed before shaped-based filtering step 240, among other possibilities. Additionally, while pore-based filtering step 280 may be helpful to further filter out false microcomedones from the results determined by application of preceding operations, step 280 may be eliminated in some embodiments, particularly for skin areas that are relatively free of other types of spots.

As described, exemplary method 200 is for a fully or partially automated method of detecting microcomedones in a captured green fluorescence image, in which the resultant image has been processed to provide a clear visual indication of detected microcomedones. It should be noted, however, that the captured green fluorescence image itself as well intermediate images in the method 200 also provide valuable information and in exemplary embodiments can be displayed, stored, communicated or further processed, in addition to or instead of the final resultant image.

For applications in which comedones are to be detected, method 200 can be readily modified so as to keep comedones in the subset of spots of interest. For instance, it should be noted that a reason for applying the size-based filtering of step 250 and the intensity-based filtering step of 260 is to differentiate between microcomedones and comedones, which will also fluoresce due to coproporphyrin III. Thus by omitting step 250 and/or 260 or adjusting one or more of the threshold values (e.g., intensity threshold value increased and/or area threshold value increased) comedones can be retained in the subset of spots of interest.

Figure 3:
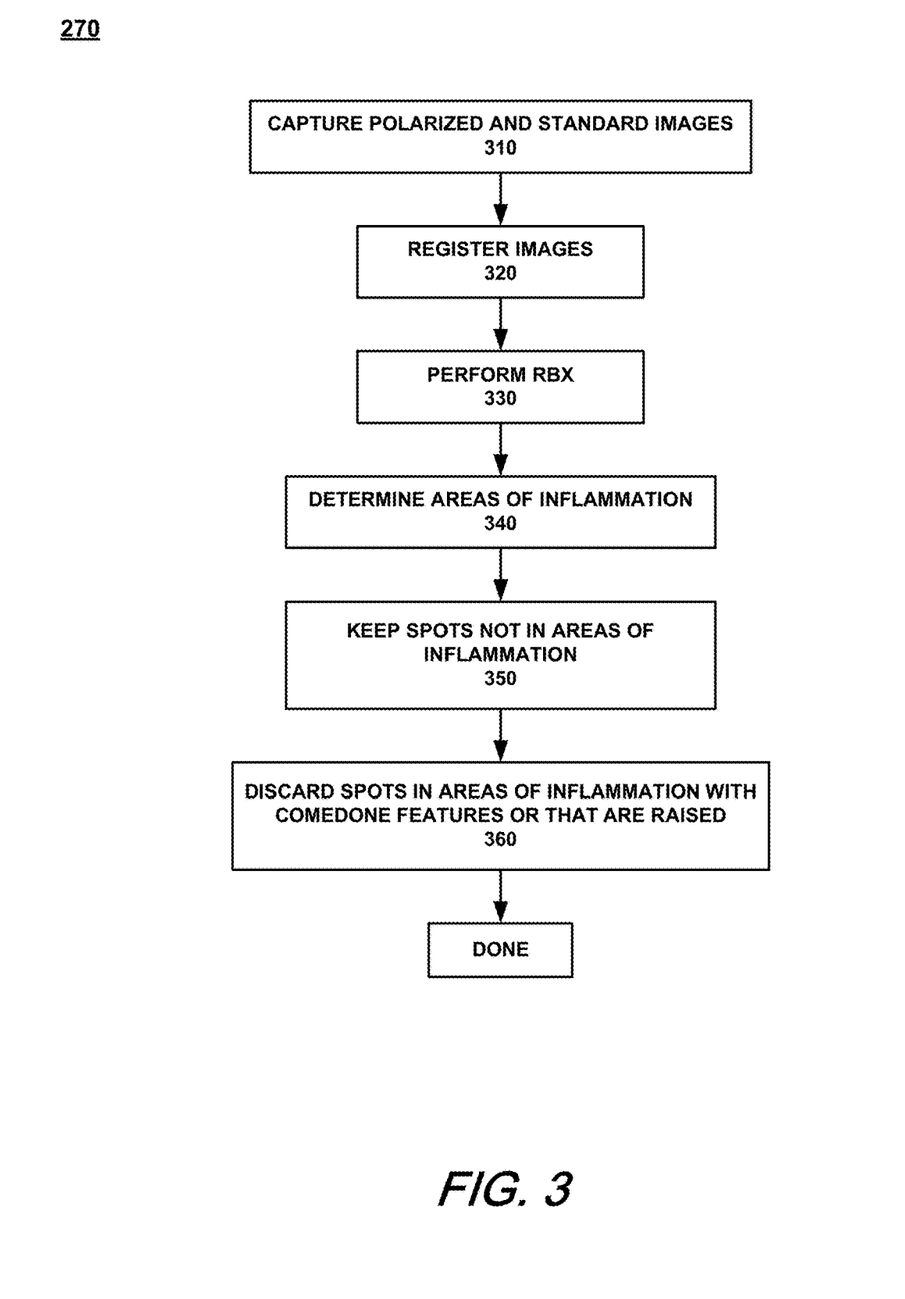
FIG. 3 is a flow chart depicting an exemplary inflammation-based filtering operation for use in detecting microcomedones.

FIG. 3 is a flow chart of an exemplary inflammation-based filtering operation, as used in step 270 of the exemplary microcomedone detection method of FIG. 2. The filtering operation starts at step 310 in which a polarized and preferably a standard white light reflection image of the subject skin area are captured. The polarized image includes a cross-polarized image, and may also include a parallel-polarized image as well. At step 320, the images are registered, such as with the use of known elastic registration techniques, with the corrected green fluorescence image.

Operation then proceeds to step 330 in which an RBX operation is performed as described in U.S. Pat. No. 8,498,460, incorporated herein by reference in its entirety. More specifically, using the cross-polarized image captured in step 310, the RBX operation generates an RBX-Red image which indicates the presence of hemoglobin and thus potential areas of inflammation. Preferably, an RBX-Brown image is generated as well.

At step 340, areas of inflammation are determined using the RBX-Red image. Additionally, areas of inflammation will appear as dark areas in the green fluorescence image. The hemoglobin around fluorescing acne absorbs the fluorescence light and appears dark relative to the background skin. The higher the concentration of hemoglobin around a lesion, the more fluorescence light the hemoglobin will absorb and the darker the area will appear. In an exemplary embodiment, areas of inflammation are determined at step 340 by combining (such as by a logical OR operation) the areas from the RBX-Red image as well as the dark areas from the green fluorescence image.

In an exemplary embodiment, the aforementioned dark areas in the green fluorescence image are detected using a thresholding technique, which is preferably preceded by one or more pre-processing steps in which the corrected green fluorescence image is flattened (background subtraction), smoothened, and/or sharpened, among other possibilities. The pre-processed image is then subjected to thresholding in which any pixels with values (which are indicative of intensity) lower than a threshold value are turned black, and any pixels with values above the threshold value are turned white. The black pixels in the resultant binary image are deemed to be representative of dark areas in the green fluorescence image, and thus areas of inflammation. A hysteresis thresholding technique may also be used, in which any pixel of the pre-processed green fluorescence image whose value is below a lower threshold value (e.g., 20%+/−10% of full scale) is turned black. The pixels surrounding the black pixels are then searched recursively and any such surrounding pixels with values lower than an upper threshold value (e.g., 40%+/−10% of full scale) are also turned black. Any pixels whose values are at or above the upper threshold value are turned white Any clusters of black pixels meeting a minimum size threshold (e.g., 150 pixels for a resolution of 650 pixels/inch) are retained, whereas those clusters not meeting this minimum size are ignored or discarded, or filled in (e.g., whitened). A shape-based filtering operation may then be applied to the remaining clusters of black pixels, so as to retain those clusters that are regularly shaped (e.g., meet a minimum solidity criterion threshold) and discarding those that do not.

While it is preferable to use a cross-polarized image and the RBX operation to produce an RBX-Red image and to determine areas of inflammation from it, as an alternative, areas of inflammation can be determined from the color in a standard white light image or from the a* component of a L*a*b* (or Lab) color space transformation of a standard white light image. Similar color-space based processing can be used as an alternative to generating an RBX-Brown image.

At step 350, any spots in the set of candidate microcomedone spots that are not located within the areas of inflammation determined in step 340 are retained in the set of candidate microcomedone spots. Any spots that are located in the areas of inflammation are analyzed at step 360 to determine whether they exhibit features of post-microcomedone lesions, namely, closed comedones (whiteheads), open comedones (blackheads), or inflammatory lesions. This analysis can be done using the RBX-Brown image generated with the RBX operation of step 330, the standard white light reflection image, and/or a parallel-polarized image captured in step 310. Blackheads, which appear as dark enlarged pores can be identified from the RBX-Brown image or the standard white light reflection image. Whiteheads, which appear as shiny white raised spots, can be identified from their color and skin surface topography in the standard white light reflectance image, the cross-polarized image and/or a parallel-polarized image (provided the subject skin is relatively dry and free of shine).

In an exemplary embodiment, the cross-polarized image is converted to the L*a*b* (or Lab) color space. In the L*a*b* color space image, whiteheads will appear as areas of brightness in the L* channel and areas of darkness in the a* channel. At or about the locations where fluorescence spots have been detected, the corresponding pixels of the color space transformed cross-polarized image are checked to determine whether they are bright in the L* channel and dark in a* channel. If so, those fluorescence spots are deemed to be whiteheads.

It should be noted that even though the cross-polarized and fluorescence images are elastically registered, it is contemplated that registration may not be perfect and that its accuracy depends largely on the amount of movement of the subject between the two images. To allow for this, it is preferred that each fluorescence spot is dilated, thereby expanding the respective search window, before looking at the corresponding L* and a* values in the color transformed cross-polarized image to determine whether or not the fluorescence spot represents a whitehead. Also, while such a color space transformation technique can also be used with a standard light image, a cross-polarized image is preferable in that it is less sensitive to shine and shadows due to illumination angles.

Whiteheads will also appear as white spots in the RBX-Red image. In any case, any spots exhibiting the features of comedones or more advanced lesions are excluded in step 360 from the set of candidate microcomedones.

In an exemplary embodiment, the image capture device is a digital video camera and multiple green fluorescence images are captured repeatedly as in the case of a video recording. In such an embodiment, the captured images are processed using all or a subset of the steps described above. Although the results attainable by performing only some of the processing steps may be somewhat less accurate (i.e., more false positives or negatives), such an embodiment provides the convenience of allowing a user to view skin and have results displayed in real- or near real-time.

A further aspect of the present disclosure relates to devices that can be used to view coproporphyrin III in skin, and thus microcomedones and comedones. In an exemplary embodiment, a dermatoscope device, such as described in U.S. Patent Application Publication No. 2014/0243685 A1 (incorporated herein by reference in its entirety), is modified in accordance with the principles of the present disclosure for this purpose. More specifically, with reference to FIG. 4, dermatoscope device 400 includes one or more illumination sources, collectively illumination source 410, surrounding an optical opening defining an optical path 420 through which skin may be viewed by a user. In the exemplary device 400, illumination source 410 emits light of a blue wavelength and a green filter 425 is arranged in line with optical path 420 for green-filtering light passing through the optical opening of device 400. In operation, illumination source 410 is activated to emit blue light to illuminate the subject skin to be viewed. Light reflected and/or emitted from the skin is viewed via path 420 through green filter 425, thereby allowing a user to view spots on the subject skin representative of coproporphyrin III, characteristic of microcomedones and comedones. In exemplary embodiments, a camera may be coupled to the dermatoscope 400 to capture images similar to the green fluorescence image described above. The captured images can then be further processed, displayed, stored and/or communicated as described above.

Figure 4:
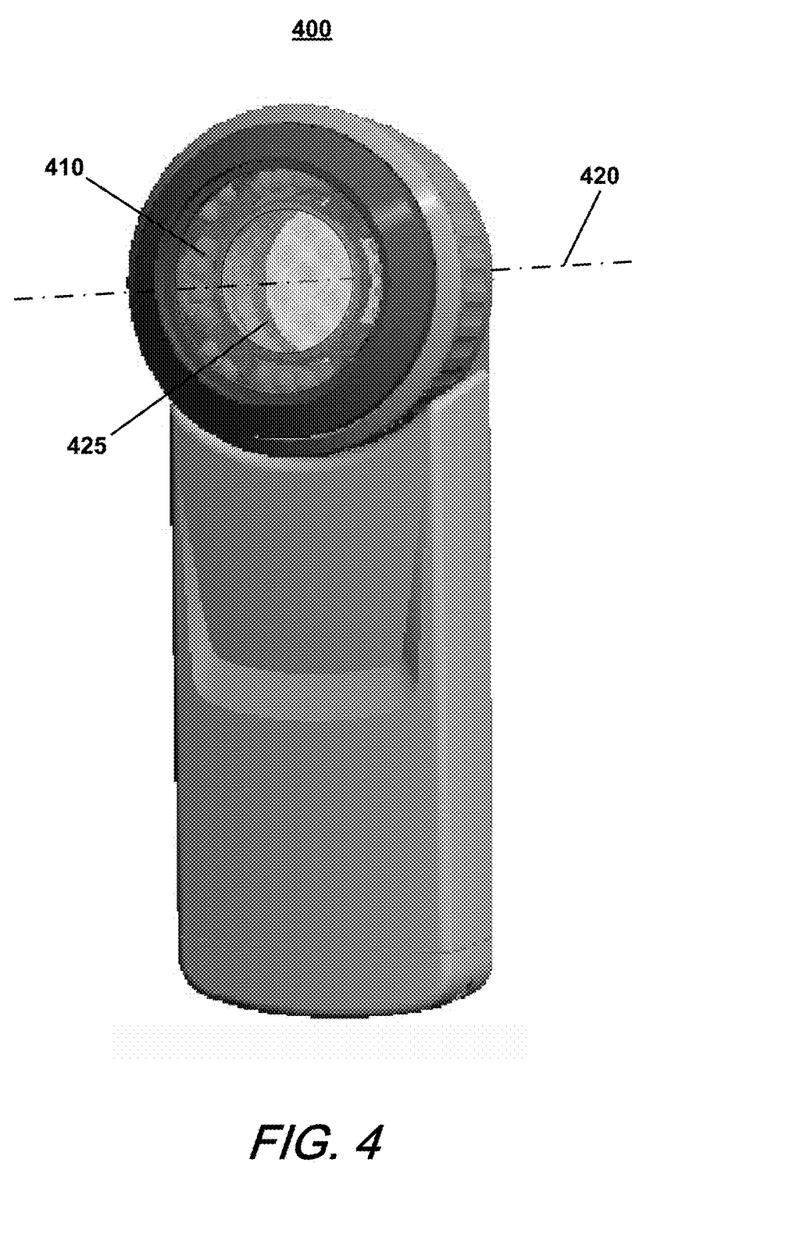
FIG. 4 is a front isometric view of an exemplary embodiment of a dermatoscopic device that can be used to visualize microcomedones.

Illumination source 410 may include, for example, a plurality of light sources such as light emitting diodes (LEDs) or the like, each of which emits a light of blue wavelength. Illumination source 410 may also be implemented with a blue-pass filter arranged in front of light sources of a broader spectrum, such as white light, so that blue light is emitted from illumination source 410 when activated.

The foregoing merely illustrates the principles of the disclosure and it will thus be appreciated that those skilled in the art will be able to devise numerous alternative arrangements which, although not explicitly described herein, embody the principles of the disclosure and are within the spirit and scope of the invention as defined by the appended claims. For example, although illustrated as single elements, each such block or step shown may be implemented with multiple blocks or steps, or various combinations thereof. It is therefore to be understood that numerous modifications may be made to the illustrative embodiments and that other arrangements may be devised without departing from the spirit and scope of the present invention as defined by the appended claims.

What is claimed is:

1. A method of detecting microcomedones in skin comprising:
    illuminating the skin with a blue light;
    capturing an image of the illuminated skin through a filter that passes light in a green-yellow band of wavelengths;
    processing the captured image to detect one or more skin areas containing a porphyrin whose fluorescence emission is primarily in an orange-red band of wavelengths, the one or more areas representing one or more possible microcomedones, wherein processing the captured image includes:
        detecting fluorescent spots in the captured image, the fluorescent spots representing the one or more skin areas containing the porphyrin; and
        selecting a subset of the detected fluorescent spots, including selecting spots having an intensity less than an intensity threshold, regular shapes, and an area smaller than a first area threshold and larger than a second area threshold that is lower than the first area threshold and at least 150 microns in diameter or 12 pixels in area, wherein the selected subset of the detected fluorescent spots includes microcomedones; and
    generating a further image of the skin indicating the subset of spots as possible microcomedones.
2. The method of claim 1, wherein processing the captured image includes:
    correcting the captured image to generate a corrected image, wherein the fluorescent spots are detected in the corrected image.
3. The method of claim 1, wherein selecting the subset of spots includes selecting spots that are not associated with inflammation or that do not have comedone features.
4. The method of claim 1 comprising detecting pores in the skin, wherein selecting the subset of spots includes selecting spots corresponding to the detected pores.
5. The method of claim 1, wherein the blue light has a center wavelength in the range of 400 nm to 410 nm.
6. The method of claim 1, wherein the filter has a center wavelength in the range of 525 nm to 575 nm.
7. The method of claim 1, wherein the intensity of a spot is determined in accordance with a mean or median pixel intensity of image pixels associated with the spot, and the intensity threshold is 60% to 80% of full scale intensity.
8. The method of claim 1, wherein the first area threshold is at least one of 70% to 90% of the median or 120% to 140% of the mean size of the subset of spots.
9. The method of claim 2, wherein correcting the captured image includes normalizing the captured image against at least one of a chromophore distribution image or an excitation image.
10. The method of claim 9, wherein the chromophore distribution image indicates the distribution in the skin of at least one of hemoglobin or melanin.
11. The method of claim 9, wherein the excitation image is an image of the skin captured while illuminating the skin with the blue light.
12. The method of claim 1 comprising comparing the captured image with a stored image.
13. The method of claim 1 comprising comparing the further image with a stored image.
14. An apparatus for detecting microcomedones comprising:
    an image capture device including a viewing opening;
    a light source arranged about the viewing opening;
    a filter for filtering light passing through the viewing opening, wherein light of a blue wavelength is emitted from the apparatus when the light source is activated, and wherein the filter passes light in a green-yellow band of wavelengths; and
    processing circuitry configured to process an image captured by the image capture device to detect one or more skin areas containing a porphyrin whose fluorescence emission is primarily in an orange-red band of wavelengths, the one or more areas representing one or more possible microcomedones, wherein processing the captured image includes:
        detecting fluorescent spots in the captured image, the fluorescent spots representing the one or more skin areas containing the porphyrin; and
        selecting a subset of the detected fluorescent spots, including selecting spots having an intensity less than an intensity threshold, regular shapes, and an area smaller than a first area threshold and larger than a second area threshold that is lower than the first area threshold and at least 150 microns in diameter or 12 pixels in area, wherein the selected subset of the detected fluorescent spots includes microcomedones,
    wherein the processing circuitry is configured to generate a further image of the skin indicating the subset of spots as possible microcomedones.

15. The apparatus of claim 14, wherein the light source comprises at least one of a blue light emitting light source or a blue filter.

16. The apparatus of claim 14, wherein the blue light has a center wavelength in the range of 400 nm to 410 nm.

17. The apparatus of claim 14, wherein the filter has a center wavelength in the range of 525 nm to 575 nm.

18. The method of claim 1, wherein the porphyrin includes coproporphyrin III.

19. The apparatus of claim 14, wherein the processing circuitry is configured to:
correct the captured image to generate a corrected image, wherein the fluorescent spots are detected in the corrected image.

20. The method of claim 1 comprising:
detecting pores in the skin; and
determining a mean or median pore size of the detected pores,
wherein selecting the subset of spots includes selecting spots corresponding to the detected pores and having an area smaller than an area threshold that is based on the mean or median pore size.

21. The apparatus of claim 14, wherein the first area threshold is at least one of 70% to 90% of the median or 120% to 140% of the mean size of the subset of spots.

22. The apparatus of claim 14, wherein selecting the subset of spots includes selecting spots that are not associated with inflammation or that do not have comedone features.

23. The apparatus of claim 14, wherein the intensity of a spot is determined in accordance with a mean or median pixel intensity of image pixels associated with the spot, and the intensity threshold is 60% to 80% of full scale intensity.

* * * * *